United States Patent
Takeuchi et al.

(10) Patent No.: US 7,473,789 B2
(45) Date of Patent: Jan. 6, 2009

(54) 9-(1',5'-DIMETHYL-1'-VINYL-4'-HEXENYL)-4-HYDROXY-7H-FURO[3,2-γ] [1] BENZOPYRAN-7-ONE AS ANTIBACTERIAL AGENT

(75) Inventors: Ryo Takeuchi, Kanagawa (JP); Tadahiro Hiramoto, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 11/661,754

(22) PCT Filed: Aug. 30, 2005

(86) PCT No.: PCT/JP2005/016177

§ 371 (c)(1), (2), (4) Date: Mar. 2, 2007

(87) PCT Pub. No.: WO2006/028024

PCT Pub. Date: Mar. 16, 2006

(65) Prior Publication Data

US 2008/0081918 A1 Apr. 3, 2008

(30) Foreign Application Priority Data

Sep. 9, 2004 (JP) ............................. 2004-262907

(51) Int. Cl.
C07D 493/04 (2006.01)

(52) U.S. Cl. ..................... 549/282; 514/455; 426/335

(58) Field of Classification Search .................. 549/282
See application file for complete search history.

(56) References Cited

FOREIGN PATENT DOCUMENTS

| EP | 1 240 832 A | 9/2002 |
|---|---|---|
| JP | 07 138250 A | 5/1995 |

OTHER PUBLICATIONS

Yu et al., LWT—Food Science and Technology, 2008, 41(3), 420-424.*
Kwon et al., "Antimicrobial constituents of *Angelica dahurica* roots," Phytochemistry, Pergamon Press, GB, vol. 44, No. 5, Mar. 1997, pp. 887-889.
Banerjee et al., "Coumarins of *Heracleum-Thomsoni* and Claisen Rearrangement of Lanatin," Phytochemistry (Oxford), vol. 19, No. 6, 1980, pp. 1256-1258.
Franke et al., "Furanocoumarins from *Dorstenia gigas*," Phytochemistry, Pergamon Press, GB, vol. 56, No. 6, Mar. 2001, pp. 611-621.
Kumar et al., "Coumarins form stem bark of *Paramignya monophylla*," Phytochemistry (Oxford), vol. 38, No. 3, 1995, pp. 805-806.
Wu et al., "Coumarins Acridone Alkaloids and a Flavone form *Citrus-Grandis*," Phytochemistry (Oxford), vol. 27, No. 2, 1988, pp. 585-587.

* cited by examiner

*Primary Examiner*—B. Dentz
*Assistant Examiner*—David E Gallis
(74) *Attorney, Agent, or Firm*—Morgan Lewis & Bockius, LLP

(57) ABSTRACT

The object of the present invention is to provide an antibacterial agent which has an improved antibacterial effect and a wider antibacterial spectrum than conventional antibacterial agents, and which is highly safe to human and the environment. This object is achieved with a novel substance 9-(1',5'-dimethyl-1'-vinyl-4'-hexenyl)-4-hydroxy-7H-furo[3,2-γ][1] benzopyran-7-one and an antibacterial agent comprising thereof.

8 Claims, No Drawings

9-(1',5'-DIMETHYL-1'-VINYL-4'-HEXENYL)-4-HYDROXY-7H-FURO[3,2-γ][1] BENZOPYRAN-7-ONE AS ANTIBACTERIAL AGENT

CROSS-REFERENCE TO RELATED APPLICATIONS

The present application is a U.S. National Phase Application of International Application PCT/JP2005/016177, filed Aug. 30, 2005, which claims the benefit of Japanese Patent Application No. 2004-262907, filed Sep. 9, 2004, each of which is incorporated by reference in its entirety.

TECHNICAL FIELD

The present invention relates to a novel compound 9-(1',5'-dimethyl-1'-vinyl-4'-hexenyl)-4-hydroxy-7H-furo[3,2-γ][1]benzopyran-7-one and an antibacterial agent comprising the novel compound. This antibacterial agent has an improved antibacterial effect for a wide range of bacterial species, is safe for human and the environment, and is tasteless and odorless by itself that it does not change the smell or the taste of the food or the like being added therewith, thus finds itself in many applications.

BACKGROUND ART

Traditionally, antibacterial agents and antiseptic agents have been used in various fields such as food products, cosmetic products, oral products, pharmaceuticals, medicated cosmetics and daily goods to prevent deterioration in quality or flavor associated with the growth of harmful microorganisms or to deal with unpleasant odors associated with the growth of microorganisms.

For example, food products are added with antiseptic agents for longer shelf life and food poisoning prevention. Oral products are added with antibacterial agents to prevent and control the growth of cariogenic bacteria and periodontal bacteria that cause tooth cavities and periodontal disease, respectively. Moreover, cosmetic products are added with antibacterial agents to control the growth of armpit odor bacteria, dandruff-causative bacteria and acne bacteria that cause armpit odor, dandruff and acnes, respectively.

However, since conventionally used antibacterial agents and antiseptic agents do not have adequate antibacterial activity or adequately wide antibacterial spectrum, little of them show satisfactory effects. In addition, even agents having antibacterial activities and wide antibacterial spectra are not always satisfactory in terms of safety that they could be great pressure on human and the environment.

For example, paraben conventionally and frequently used as an antiseptic agent in cosmetic products has a narrow antibacterial spectrum and a weak activity and thus has not always been a satisfactory antibacterial agent. Triclosan known as an antibacterial substance with a stronger antibacterial activity and a wider antibacterial spectrum harbors a chlorine atom in its molecule and thus limited of its use in products for the concern about the effects on the environment and human body.

In beverage industry, heat sterilization is employed to prevent reduction of commercial value associated with proliferation of bacteria. The heat sterilization, however, has a problem of greatly deteriorating the flavor of the product. Thus, in addition to minimal heat treatment, addition of a substance having an antibacterial effect such as sucrose fatty acid ester is proposed to deal with proliferation of bacteria. The ester, however, is poorly dispersed in an acidic region and likely to crystallize, causing turbidity and sediment in an acidic beverage and thus pointed out of its disadvantage of reducing the commercial value of the product.

Moreover, due to the recent increase of sanitary and safety concerns by the consumers, highly safe antibacterial agents with higher antibacterial actions and wider antibacterial spectra have been desired especially for products that directly touches human body such as food products, oral products and cosmetic products.

DISCLOSURE OF THE INVENTION

Thus, the object of the present invention is to provide an antibacterial agent which is unharmful and safe for human and the environment and which is not a chloride compound, with a stronger antibacterial activity and a wider antibacterial spectrum compared to conventional antibacterial agents.

In order to obtain an antibacterial activity substance which has adequate antibacterial activity and adequately wide antibacterial spectrum and which does not contain chlorine atom that is seen as a problem in terms of safety, the present inventors have studied a lot and found that a novel substance 9-(1',5'-dimethyl-1'-vinyl-4'-hexenyl)-4-hydroxy-7H-furo[3,2-γ][1]benzopyran-7-one is superior to conventional antibacterial substances, thereby accomplishing the present invention.

Thus, according to the present invention, an antibacterial agent comprising a novel compound 9-(1',5'-dimethyl-1'-vinyl-4'-hexenyl)-4-hydroxy-7H-furo[3,2-γ][1]benzopyran-7-one is provided to solve the above-described problem. In addition, a food product, a cosmetic product, an oral product and a pharmaceutical product containing this novel compound are also provided.

Furthermore, according to the present invention, a method for producing a novel compound 9-(1',5'-dimethyl-1'-vinyl-4'-hexenyl)-4-hydroxy-7H-furo[3,2-γ][1]benzopyran-7-one, comprising the steps of: dissolving 4-(1',5'-dimethyl-1'-vinyl-4'-hexeneoxy)-7H-furo-[3,2-y][1]benzopyran-7-one in a high-boiling organic solvent; and agitating while heating in an inert gas atmosphere, and a method for producing a novel compound 9-(1',5'-dimethyl-1'-vinyl-4'-hexenyl)-4-hydroxy-7H-furo[3,2-γ][1]benzopyran-7-one, comprising the steps of: dissolving a compound obtained by protecting a phenolic hydroxyl group of 3-[6'-(3'',7''-dimethyl-2'',6''-octadieneoxy)-4'-hydroxy-5'-benzofuranyl]-propenoic acid alkylester with a protective group in a high-boiling organic solvent; agitating while heating in an inert gas atmosphere; and removing the protective group are provided.

According to the present invention, a novel antibacterial agent comprising 9-(1',5'-dimethyl-1'-vinyl-4'-hexenyl)-4-hydroxy-7H-furo[3,2-γ][1]benzopyran-7-one as an active element, and further an antibacterial agent having an antibacterial property that has never been realized can be provided.

BEST MODE FOR CARRYING OUT THE INVENTION

Hereinafter, the present invention will be described in more detail.

"Antibacterial agent" as used herein refers to an improved agent having the property as antiseptic and disinfectant agents, comprising a novel compound 9-(1',5'-dimethyl-1'-vinyl-4'-hexenyl)-4-hydroxy-7H-furo[3,2-γ][1]benzopyran-7-one (Formula (1) below), or an agent comprising the novel compound as an active element.

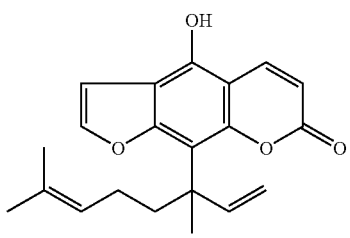

Formula (1)

In Formula (1) above, since an asymmetric carbon exists, it may exist as a single optically-active substance ((1'R)-9-(1', 5'-dimethyl-1'-vinyl-4'-hexenyl)-4-hydroxy-7H-furo[3,2-γ][1]benzopyran-7-one or (1'S)-9-(1',5'-dimethyl-1'-vinyl-4'-hexenyl)-4-hydroxy-7H-furo[3,2-γ][1]benzopyran-7-one), or as an optically-active substance mixture thereof.

The compound represented by Formula (1) above may be produced, for example, by dissolving the compound (4-(1', 5'-dimethyl-1'-vinyl-4'-hexeneoxy)-7H-furo-[3,2-γ][1]benzopyran-7-one) represented by Formula (2) in a high-boiling organic solvent such as benzyl alcohol, and agitating while heating in an inert gas atmosphere such as nitrogen and argon.

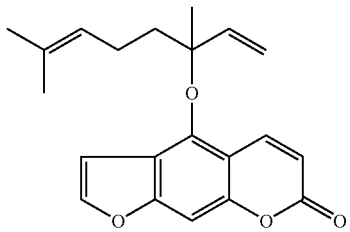

Formula (2)

In addition, the compound represented by Formula (1) may also be obtained by dissolving the compound represented by Formula (3) below (3-[6'-(3",7"-dimethyl-2",6"-octadieneoxy)-4'-hydroxy-5'-benzofuranyl]-propenoic acid alkylester having a phenolic hydroxyl group protected with a protective group ($R^1$)) in a high-boiling organic solvent such as benzyl alcohol, and heating at a high temperature in an inert gas atmosphere such as nitrogen and argon to obtain an intermediate (Formula (4), 9-(1',5'-dimethyl-1'-vinyl-4-hexenyl)-4-hydroxy-7H-furo-[3,2-γ][1]benzopyran-7-one) having a phenolic hydroxyl group protected with a protective group ($R^1$)), which is then subjected to acid treatment to deprotect the protective group represented by $R^1$.

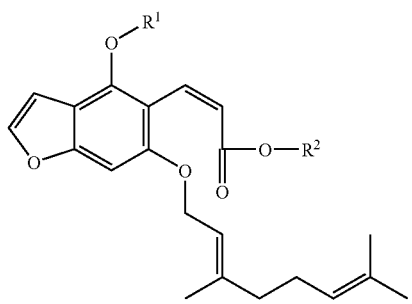

Formula (3)

[wherein, $R^1$ is a protective group such as a methyl group, a methoxymethyl group and a tert-butyldimethyl silyl group, which forms ether linkage with a novel compound 7H-furo [3,2-γ][1]benzopyran-7-one skeleton; and $R^2$ is an alkyl group such as a methyl group and an ethyl group.]

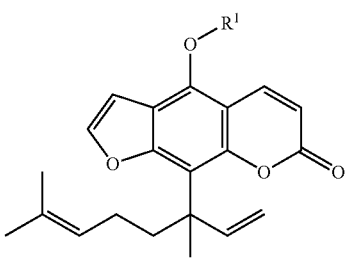

Formula (4)

[wherein, $R^1$ is the same as $R^1$ in Formula (3).]

When the compound represented by Formula (2) is used to obtain the novel compound of the invention represented by Formula (1), conditions for heat reaction, namely, a high-boiling organic solvent and temperature can be suitably adjusted. Preferably, benzyl alcohol or dimethyl sulfoxide is used as the high-boiling organic solvent. Also, natural fat such as rice cooking oil, palm oil and corn oil may be used. The reaction temperature is 100° C.-180° C., preferably 130° C.-160° C.

Atmospheric pressure is preferable.

The reaction time is preferably 1-7 hours, and more preferably 3-6 hours.

The concentration of the compound of Formula (2) above upon heat treatment is preferably 0.001-50% by weight and more preferably 10-30% by weight.

The compound of Formula (3) above may be used to suitably adjust conditions for obtaining the novel compound of the invention shown in Formula (1), namely, conditions for heat reaction and deprotection. The heat reaction conditions may be the same as those used for Formula (2) above. Preferably, the deprotection reaction of the protective group represented by $R^1$ is carried out in an anhydrous condition.

The thus-obtained novel compound of the present invention exerts improved antibacterial effects against various bacteria. Examples of these bacteria include cariogenic bacteria, periodontal bacteria, acne bacteria, abscess bacteria, armpit odor bacteria, dandruff-causative bacteria, resident skin bacteria, putrefactive bacteria, food poisoning bacteria, gastric ulcer-causative bacteria, *staphyrococcus aureus* and heat-resistant acidophilic bacteria, preferably cariogenic bacteria, periodontal bacteria, acne bacteria, abscess bacteria, putrefactive bacteria, *staphyrococcus aureus* and heat-resistant acidophilic bacteria.

Specific examples of these bacteria are as follows.

Cariogenic bacteria; *Actinomyces naeslundii, Actinomyces viscosus, Streptococcus mutans*.

Periodontal bacteria; *Fusobacterium nucleatum, Prevotella intermedia, Porphyromonas gingivalis*.

Acne bacteria; *Propionibacteriun acnes*.

Abscess bacteria; *Bacteroides fragilis*.

Armpit odor bacteria; *Corynebacterium xerosis*.

Dandruff-causative bacteria; *Malassezia furfur*.

Resident skin bacteria; *Staphyrococcus epidermidis, Corynebacterium minutissimum*.

Putrefactive bacteria; *Bacillus subtilis*.

Food poisoning bacteria; *Vibrio parahaemoliticus, Campylobacter jejuni.*

Gastric ulcer-causative bacteria; *Helicobacter pylori.*

*Staphyrococcus aureus;. Staphyrococcus aureus*

Heat-resistant acidophilic bacteria; *Alicyclobacillus acidocaldarius* (NCIMB), *Alicyclobacillus acidoterrestris* (NCIMB).

The novel compound of the invention can directly be added as an antibacterial agent to food products and the like. The novel compound of the invention can be dissolved or dispersed in a suitable liquid carrier (e.g., ethanol, aqueous ethanol, benzyl alcohol, medium-chain triglyceride (MCT), etc.), or mixed with or adsorbed to a suitable powder carrier (e.g., polysaccharides, processed starch, active carbon, silica gel, etc.) to be used as an antibacterial agent. In some cases, an emulsifying agent, a dispersant, a suspending agent, a spreading agent, a penetrant, a wetting agent or a stabilizer can be added to formulate an emulsion, a hydrating agent, powder or a tablet to be used as an antibacterial agent for food products, cosmetic products or oral products.

Furthermore, the novel compound of the invention may be mixed with a blending agent or a combination of two or more blending agents such as a filler, an antioxidant, a pigment, known antiseptic and antibacterial agent, a deodorant substance, a surfactant, a flavoring ingredient, a stabilizer, an absorbent (calcium chloride, highly water absorbent polymer, etc.) and an excipient (lactose, etc.) to prepare a characteristic antibacterial agent of the invention.

For example, when the antibacterial composition of the invention is incorporated into a cosmetic product, a toiletry product, an oral product or the like, a flavoring ingredient is preferably added to the antibacterial composition so that it can create an image of cleanliness. When the antibacterial composition of the invention is incorporated into a food product, a flavoring ingredient is also preferably added to the antibacterial composition so that it can complement the flavoring ingredient which was lost from the food product for the various reasons. A surfactant is preferably added to the antibacterial composition of the invention so that when the antibacterial composition is added to the product, the surfactant enables the antibacterial composition to dissolve or disperse in the product effectively. A deodorant substance is preferably added to the antibacterial composition of the invention so that it can remove unpleasant odor as well as restrain the proliferation of the bacteria which cause such odor. A filler is preferably added to the antibacterial composition of the invention so that the antibacterial composition can be used in powdery form as well as liquid form. A known antiseptic and/or antibacterial agent is preferably added to the antibacterial composition of the invention in order to exert antibacterial effect against the broadest possible range of bacteria.

The amount of the blending agent is not limited as long as the primary object is achieved.

Examples of fillers include saccharine, polysaccharides, processed starch, casein, gelatin, carboxymethyl cellulose (hereinafter, referred to as "CMC") and lecithin.

Examples of antioxidants include butylhydroxytoluene, butylhydroxyanisole, citric acid, biofulvic acid, glutathione, selenium, lycopene, vitamin A, vitamin E, vitamin C as well as pyrrolopyrrole derivatives, free radical scavengers obtained from various plant extracts, superoxide dismutase, and enzymes with antioxidant property such as glutathione peroxidase.

As pigments, dye, lake, synthetic pigment such as organic color (tarcolor) and natural pigments are known, and examples thereof specifically include hibiscus pigment, huckleberry pigment, plum pigment, laver pigment, dewberry pigment, grape juice pigment, blackberry pigment, blueberry pigment, mulberry pigment, morello cherry pigment, red currant pigment, loganberry pigment, powdered paprika, malt extract, rutin, flavonoid, red cabbage pigment, red radish pigment, Adzuki bean pigment, turmeric pigment, olive tea, cowberry pigment, powdered chlorella, saffron pigment, perilla pigment, strawberry pigment, chicory pigment, pecan nut pigment, monascus pigment, safflower pigment, purple sweet potato pigment, lac pigment, spirulina pigment, onion pigment, tamarind pigment, capsicum pigment, gardenia pigment, lithospermi radix pigment, rose wood pigment, krill pigment, orange pigment, carrot carotene, caramel, titanium dioxide, sodium iron chlorophyllin, riboflavin, potassium norbixin, sodium norbixin, amaranth, erythrosin, new coccine, phloxine B, rose bengal, acid red, tartrazine, sunset yellow, fast green, brilliant blue, indigo carmine, lake red C, lithol red, rhodamine, phloxine, indigo, ponceau, orange I, Sudan blue, mica, talc, calcium carbonate, kaolin, silicic acid anhydride, aluminum oxide, Bengara, ferric oxide, ultramarine, carbon black, zinc oxide, isinglass, bismuth oxychloride, boron nitride, photochromic color, particulate complex powder (hybrid fine powder) and synthetic mica.

Examples of known antiseptic agents and antibacterial agents include benzoic acid, sodium benzoate, isopropyl paraoxybenzoate, isobutyl paraoxybenzoate, ethyl paraoxybenzoate, methyl paraoxybenzoate, butyl paraoxybenzoate, propyl paraoxybenzoate, sodium sulfite, sodium hyposulfite, potassium pyrosulfite, sorbic acid, potassium sorbate, sodium dehydroacetate, thujaplicin, udo (*Aralia cordata*) extract, storax extract, artemisia capillaris extract, oolong tea extract, soft roe protein extract, enzyme-degraded job's tear extract, tea catechins, apple polyphenol, pectin-degrading substance, chitosan, lysozyme and e-polylysine.

Examples of known deodorants include deodorants with desulfurization action (e.g., iron sulfate such as ferrous sulfate or iron hydrochloride), deodorants with chemical action (e.g., acidic agent, alkaline agent, oxidant or reductant), deodorants with addition/condensation action (addition agent: (meta)acrylic acid ester, ester maleate, etc.; condensation agent: glyoxysal, etc.), deodorants with ion exchange action (e.g., amphoteric agent, cation agent and anion agent for ion exchange resin), deodorants with drug impregnated adsorption action (alkaline or acidic impregnated active carbon and mixture of active carbon and chemical reactant), deodorants with adsorption action (e.g., neutral active carbon, fibrous carbon adsorbent, zeolite and porous adsorbents such as activated clay), deodorants with absorbing action (e.g., organic solvents such as alcohol and hexane, water and surfactant), deodorants with enzyme action (e.g., digestive enzyme, good oral bacteria LS-1 lactic acid bacteria, yeast and soil bacteria), deodorants with antiseptic/sterilizing action (e.g., chloramine T, parabens and phenols), polyphenol deodorants (e.g., persimmon polyphenol, tea catechin, rosemary extract, oolong tea extract, tansy extract, *Ouercus salicina* leaf extract and rice bran/soybean roasted extract), cyclodextrin, champignon extract, Rooibos extract, sodium iron chlorophin, active carbon and zeolite.

Preferably, surfactant is one or a combination of two or more surfactants of nonionic type, specifically polyoxyethylenealkylether and fatty acid alkylol amide, or acylglutamic acid. Examples of polyoxyethylenealkylether include polyoxyethylenestearyl and polyoxyethylene hydrogenated castor oil. An example of fatty acid alkylol amide includes coconut oil fatty acid diethanolamide. Examples of acylglutamic acid type include glutamic acid ester of saturated and unsaturated fatty acid with a carbon number of 12-18, or a mixture thereof such as coconut oil fatty acid, hydrogenated coconut oil fatty acid, palm oil fatty acid, hydrogenated palm oil fatty acid, tallow fatty acid and hydrogenated tallow fatty acid, and specifically include N-coconut oil fatty acid acyl-L-glutamic acid triethanolamine, lauroyl-L-glutamic acid triethanolamine, N-coconut oil fatty acid acyl-sodium L-glutamate, N-lauroyl-sodium L-glutamate, N-myristoyl-sodium L-glutamate, N-coconut oil fatty acid/hydrogenated tallow fatty acid acyl-sodium L-glutamate and N-coconut oil fatty acid acyl-potassium L-glutamate.

Furthermore, a flavoring ingredient (flavor or fragrance) may be blended with the antibacterial agent. As a result, aroma can be added to further improve usability.

The blending quantity of a flavoring ingredient varies on the application and usage of the antibacterial agent, but usually 0.001-20% by weight of the antibacterial agent is preferable.

Examples of flavors used with the present invention include synthetic flavoring ingredients such as esters, alcohols, aldehydes, ketones, acetals, phenols, ethers, lactones, furans, hydrocarbons and acids as well as natural flavoring ingredients.

Examples of fragrances used with the present invention include hydrocarbons, alcohols, phenols, aldehydes and/or acetals, ketones and/or ketals, ethers, synthetic musks, acids, lactones, esters, halogen-containing compounds as well as natural flavoring ingredient.

Other than the above flavors and fragrances, flavoring ingredients described in "Field survey of food flavoring ingredient compounds used in Japan" (2000, Health Science Study Report; Japan Flavor and Fragrance Materials Association, issued March 2001); "Synthetic flavoring ingredient chemicals and product knowledge" (Genichi Indo, issued Mar. 6, 1996, Chemical Daily Co., Ltd.); and "Perfume and Flavor Chemicals (Aroma Chemicals) 1,2" (Steffen Arctender (1969)) may be used.

These flavors and fragrances may be used alone or in combination of two or more.

Commercially available flavors and fragrances may also be used. Each of them may be synthetic or derived from a natural source such as a plant. Essential oils, resinoid, balsam, absolute, concrete and tincture may be prepared by a known method.

The antibacterial agent of the present invention may be added to and blended with, for example, a food product, a cosmetic product (a fragrance product, a skin-care cosmetic, a hair-care cosmetic, a toiletry product, a bath additive, a body-care product, a detergent, a softener, an aromatic deodorant), an oral product and a pharmaceutical product but not limited thereto. Preferably, the antibacterial composition of the present invention may be added to and blended with a food product and an oral product.

Examples of the above food products include beverages such as fruit beverage, non-fruit beverage, tea beverage, lactic acid beverage and powder beverage, frozen desserts such as ice cream, sherbet and ice dessert, desserts such as pudding, jelly, Bavarian cream and yogurt, confectioneries such as gum and candy and fish-paste products.

Examples of the above fragrance product include perfume, eau de toilette, eau de cologne and shower cologne.

Examples of the above skin-care cosmetics include skin cream, cleansing cream, skin lotion, after-shaving lotion, foundation, lipstick and talcum powder.

Examples of the above hair-care cosmetics include hair-care products such as shampoo, rinse, conditioner, rinse-in-shampoo and treatment agent, hair styling agents such as pomade, hair tonic, hair liquid and hair gel, hair-growth agent, hair dye and cold wave lotion.

Examples of the above toiletry products include cosmetic soap, bath soap and transparent soap.

Examples of the above detergents include a powdered fabric detergent, a liquid fabric detergent, a softener, a kitchen detergent, a toilet detergent, a bathroom detergent, a glass cleaner and a mildew remover.

Examples of the above bath additives include bath powder, bath cake, bubble bath cake, bath oil and bubble bath.

Examples of the above aromatic deodorants include a gel aromatic deodorant, a mist aromatic deodorant and an impregnated aerosol aromatic deodorant.

Examples of the above pharmaceuticals include a tablet, a liquid drug, a capsule-type drug and a granular drug.

Examples of the above oral products include a mouth wash, a tooth paste, an oral care gum and an oral care candy.

The amount of additives added to or blended with the above-described antibacterial agent greatly varies depending on the subject ("the subject" may be the final product or the raw material of the final product) to be added and bacteria to be aimed, but usually, an amount of 0.0000001-50% by weight of the subject is preferable. When the amount is 0.0000001% by weight or less, the antibacterial activity ability will be inadequate, and when 50% by weight or more, the antibacterial activity ability is adequate but disadvantageous in economic terms. Most preferably, the amount is 0.00001-10% by weight of the subject.

The novel compound of the invention 9-(1',5'-dimethyl-1'-vinyl-4'-hexenyl)-4-hydroxy-7H-furo[3,2-γ][1]benzopyran-7-one shows strong antibacterial effects against, for example, cariogenic bacteria, periodontal bacteria, acne bacteria, armpit odor bacteria, dandruff-causative bacteria, resident skin bacteria, abscess bacteria and food poisoning bacteria.

Food poisoning bacteria lead to rottenness and deterioration of food products, thereby greatly reducing the commercial value of the product. Moreover, as the bacteria proliferate, toxic is produced in the product, having serious adverse effect on those who eat the product. Thus, by adding the antibacterial agent containing the novel compound of the invention to a food product, longer shelf-life and prevention of food poisoning can be achieved.

Cariogenic bacteria cause tooth caries. Periodontal bacteria cause periodontal disease. In addition, these bacteria orally proliferate and become a source of bad breath. Thus, the antibacterial agent of the invention can be contained in oral products to prevent tooth cavities, periodontal disease and bad breath.

The antibacterial agent of the invention can be contained in various cosmetic products and the like to control proliferation of dandruff-causative bacteria, acne bacteria, armpit odor bacteria and abscess bacteria, expecting its effects in deodorant, dandruff prevention and acnes prevention.

EXAMPLES

Hereinafter, the present invention will be described in more detail with reference to Examples and comparative examples, which do not limit the present invention.

The compounds in Examples were identified using the following devices.

Proton NMR, carbon NMR: Instrument DRX500 (BRUKER BIOSPIN K.K)

MS: M-2000(Hitachi Instruments Service Co., Ltd.)

Example 1

Synthesis of 9-(1',5'-dimethyl-1'-vinyl-4'-hexenyl)-4-hydroxy-7H-furo[3,2-γ][1]benzopyran-7-one (Process using Formula (2) as a starting material)

50 mg of 4-(1',5'-dimethyl-1'-vinyl-4'-hexeneoxy)-7H-furo-[3,2-γ][1]benzopyran-7-one (Formula (2)) (0.148 mmol) was dissolved in 10 ml dimethylsulfoxide, and agitated while heating in a nitrogen atmosphere at 140° C. for 3 hours. The reaction solvent was cooled to room temperature, transferred to 10 ml water, and extracted with ethyl acetate. The organic phase was washed with water and saturated brine, dried with sodium sulfate and concentrated. 60 mg of the concentrate was purified by silica gel column chromatography to obtain the intended 9-(1',5'-dimethyl-1'-vinyl-4'-hexenyl)-4-hydroxy-7H-furo[3,2-γ][1]benzopyran-7-one for 1 mg (0.074 mmol).

Example 2

Synthesis of 9-(1',5'-dimethyl-1'-vinyl-4'-hexenyl)-4-hydroxy-7H-furo[3,2-γ][1]benzopyran-7-one (Process via Formula (3) (wherein, $R^1$ is methoxymethyl group and $R^2$ is methyl group))

8.3 g of 4-hydroxy-7H-furo[3,2-γ][1]benzopyran-7-one (41.0 mmol) was suspended in 200 ml anhydrous tetrahydrofuran, and 2.46 g of sodium hydride (61.5 mmol) was added in four additions while ice-cooling. 4.59 g of methoxy methyl chloride was added and agitated at room temperature for 3 hours. While ice-cooling, 1 ml acetic acid, then 100 ml ethyl acetate were added and continued agitation. After leaving for a while, the ethyl acetate phase was separated, washed with distilled water and brine, and dried with magnesium sulfate. After concentrating ethyl acetate, the concentrated residue was purified by silica gel column chromatography, thereby obtaining 4-methoxymethoxy-7H-furo[3,2-γ][1]benzopyran-7-one for 10.0 g (40.6 mmol).

3.44 g of 4-methoxymethoxy-7H-furo[3,2-γ][1]benzopyran-7-one (14.0 mmol) was dissolved in 60 ml anhydrous dimethyl formamide, 0.83 g of sodium methoxide (15.4 mmol) was added while ice-cooling and continued agitation. After agitation at room temperature for 20 minutes, 2.6 ml 1-chloro-3,7-dimethyl-2,6-octadiene (14 mmol) was dropped while ice-cooling. After dropping, agitation was carried out for 5 hours while slowly returning to room temperature. 60 ml ethyl acetate and 140 ml n-hexane were added and, while ice-cooling, 100 ml of water was added and the resultant agitated. After separation, the water phase was extracted with ethyl acetate twice, and together with the organic phase washed with brine twice. After drying the organic phase with sodium sulfate, the organic solvent was concentrated, thereby obtaining a concentrate. The obtained concentrated residue was purified by silica gel column chromatography, thereby obtaining the intended 3-[6'-(3'',7''-dimethyl-2'',6''-octadieneoxy)-4'-methoxymethoxy-5-benzofuranyl]-propenoic acid methylester (in Formula (3), $R^1$ is a methoxymethyl group and $R^2$ is a methyl group) for 3.77 g (9.1 mmol).

3.0 g of the obtained 3-[6'-(3'',7''-dimethyl-2'',6''-octadieneoxy)-4'-methoxymethoxy-5-benzofuranyl]-propenoic acid methyl ester (7.24 mmol) was dissolved in 28 g of dried dimethylsulfoxide, and agitated under nitrogen stream at 140° C. for 5 hours. After the agitation, temperature was cooled to room temperature and the reaction solution was diluted in water. The resultant was extracted with a mixed solvent of ethyl acetate and n-hexane. The organic phase was washed with water and saturated brine, and then dried with sodium sulfate. The residual obtained by concentrating the organic solvent was purified by silica gel column chromatography to obtain the intended 9-(1',5'-dimethyl-1'-vinyl-4'-hexenyl)-4-methoxymethoxy-7H-furo-[3,2-γ][1]benzopyran-7-one (in Formula (4), $R^1$ is a methoxymethyl group) for 1.8 g (4.7 mmol). 1.7 g of the obtained 9-(1',5'-dimethyl-1'-vinyl-4'-hexenyl)-4-methoxymethoxy-7H-furo-[3,2-γ][1]benzopyran-7-one (4.4 mmol) was dissolved in 30 ml of 50% aqueous acetic acid. A catalytic amount of sulfuric acid was added, and the resultant heated to reflux for 30 minutes. The temperature was cooled to room temperature, the reaction solution was transferred into water and extracted with toluene. The toluene phase is washed with water, neutralized in aqueous sodium carbonate, washed with saturated brine and dried with sodium sulfate. The residual obtained by concentrating the toluene phase was purified by silica gel column chromatography to obtain the intended 9-(1',5'-dimethyl-1'-vinyl-4'-hexenyl)-4-hydroxy-7H-furo-[3,2-γ][1]benzopyran-7-one (Formula (1)) for 1.19 g (3.52 mmol).

Spectrum data of the obtained novel compound was as follows. $^1$H-NMR d(CDC13): 8.28(1H,d,J=9.7 Hz) 7.57(1H, d,J=2.4 Hz) 7.26(1H,s) 6.97(1H,d,J=2.4 Hz) 6.44(1H,dd, J=10.9, 17.2 Hz) 6.29(1H,d,J=9.8 Hz) 5.02(1H,tt,J=1.37, 6.86 Hz) 4.99(1H,dd,J=10.7, 1.09 Hz) 4.98(1H,dd,J=17.2, 1.1 Hz) 2.42(1H,ddm,J=1.92, 5.21 Hz) 1.94-1.87 (2H,m) 1.81(3H,s) 1.74-1.65(1H,m) 1.56(3H,s) 1.38(3H,s)$^{13}$C-NMR d(CDC13): 17.34, 23.91, 25.59, 26.43, 40.33, 44.54, 102.58, 104.91, 110.28, 111.10, 111.38, 113.45, 124.60, 131.07, 140.00, 144.13, 147.29, 150.62, 156.69, 162.01 EIMS(m/z) [M]+338.

As to the structure of the compound above, HMBC (1H-Detected Multiple-bond Heteronuclear Multiple Quantum Coherence Spectrum) was determined. The then-confirmed curves of $^2J_{CH}$ and $^3J_{CH}$ between the side chain and 7H-furo [3,2-γ][1]benzopyran-7-one skeleton are shown below.

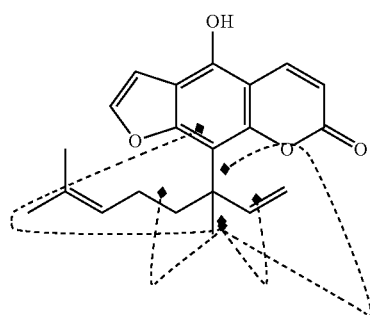

Formula (5)

Example 3

Preparation of antibacterial agent (water-soluble antibacterial agent)

500 mg of 9-(1',5'-dimethyl-1'-vinyl-4'-hexenyl)-4-hydroxy-7H-furo[3,2-γ][1]benzopyran-7-one obtained in Example 2 was dissolved in 99.5% ethanol to prepare 10 ml ethanol solution, which was used as an antibacterial agent of the present example.

Example 4

Preparation of antibacterial agent (oil-soluble antibacterial agent)

500 mg of 9-(1',5'-dimethyl-1'-vinyl-4'-hexenyl)-4-hydroxy-7H-furo[3,2-γ][1]benzopyran-7-one obtained in Example 2 was dissolved in medium-chain triglyceride (MCI) to prepare a 0.2% MCT solution.

Example 5

Determination of Minimum Inhibitory Concentration (MIC)

Minimum inhibitory concentration (MIC) was determined by Agar Dilution Test (ADT).

Samples were dissolved in ethanol or water (according to solubility of each sample) to carry out two-fold serial dilution. A hundred μl of the resultant was added to a 10 ml sterilized agar medium (skin-related bacteria and standard bacteria in Mueller-Hinton Medium (Difco), yeast and filamentous bacteria in Sabroud Medium (Difco) and anaerobic bacteria in Trypticase Soy agar(BBL)), well agitated, transferred to a 9 cmf petri dish and immobilized at room temperature. To this petri dish, a 27-spot microplanter MIT-P from Sakuma Seisakusho, LTD. was used to spot $1 \times 10^5$ cfu (colony forming unit) of skin-related bacteria and standard bacteria, and the resultants were cultured at 37° C. for 18 hours. Yeast and filamentous bacteria were spotted for 5000 cfu (except Cg-1 was 50~100 cfu) and cultured at 27° C. for 72 hours. Anaerobic bacteria were cultured at 37° C. for 72 hours under anaerobic conditions (using BBL gas pack anaerobic system). After completion of cultivation, growth of each bacterium was compared with that in a petri dish with alcohol alone (blank). A concentration of a sample without a bacterium growth was determined as the minimum inhibitory concentration (MIC).

As comparative substances, butylparaben (BPHB) and triclosan were determined as well. Results are as follows.

TABLE 1

|  | Triclosan | Butylparaben | Antibacterial agent of the present invention |
|---|---|---|---|
| Se-1 | 1.6 | 200 | 3.1 |
| Se-2 | 1.6 | 200 | 3.1 |
| Cm-1 | 1.6 | 200 | 3.1 |
| Cx-2 | 3.1 | 50 | 3.1 |
| Mf-1 | 1.6 | 100 | 3.1 |
| Sa-3 | 1.6 | 100 | 3.1 |
| Bs-1 | 0.78 | 200 | 3.1 |
| Se-3 | 1.6 | 200 | 3.1 |
| Sa-4 | 1.6 | 200 | 3.1 |
| Pa-2 | — | 100 | 3.1 |
| Pa-3 | — | 100 | 3.1 |
| Bf-1 | — | 50 | 1.6 |
| Su-1 | — | 200 | 6.3 |
| Fn-1 | — | 100 | 1.6 |
| Pg-1 | — | 50 | 1.6 |
| Pt-1 | — | 100 | 1.6 |
| Aa-1 | — | 100 | 3.1 |
| Av-1 | — | 100 | 3.1 |

* Each numeric represents unit ppm

TABLE 2

Test bacteria (Code list of test bacteria used in Examples)

| Code | Bacteria | Note |
|---|---|---|
| Skin-related bacteria | | |
| Se-1 | *Staphyrococcus epidermidis* JCM 2414 | Resident skin bacteria |
| Se-2 | *Staphyrococcus epidermidis* var. h-6 Takasago isolate | Resident skin bacteria |
| Se-3 | *Staphyrococcus epidermidis* ATCC 12228 | Resident skin bacteria |
| Cm-1 | *Corynebacterium minutissimum* IFO 15361 | Resident skin bacteria |
| Cx-2 | *Corynebacterium xerosis* JCM 1324 | Armpit odor bacteria |
| Mf-1 | *Malassezia furfur* IFO 0656 | Dandruff-causative bacteria (yeast) |
| Sa-3 | *Staphylococcus aureus* 209P IAM 12082 | *Staphylococcus aureus* |
| Sa-4 | *Staphylococcus aureus* ATCC 6538 | *Staphylococcus aureus* |
| Standard bacteria | | |
| Bs-1 | *Bacillus subtilis* PCI 219 IFO 3134 | Putrefactive bacteria |
| Anaerobic bacteria | | |
| Pa-2 | *Propionibacterium acnes* JCM 6473 | Acne bacteria |
| Pa-3 | *Propionibacterium acnes* ATCC 6919 | Acne bacteria |
| Bf-1 | *Bacteroides fragilis* GM 7000 JCM 5560 | Abscess bacteria |
| Su-1 | *Streptococcus mutans* JCM 5175 | Cariogenic bacteria |
| Fn-1 | *Fusobacterium nucleatum* JCM 6328 | Periodontal bacteria |
| Pt-1 | *Prevotella intermedia* JCM 6322 | Periodontal bacteria |
| Pg-1 | *Porphyromonas gingivalis* JCM 8525 | Periodontal bacteria |
| Aa-1 | *Actinomyces naeslundii* JCM 8350 | Cariogenic bacteria |
| Av-1 | *Actinomyces viscosus* JCM 8352 | Cariogenic bacteria |

According to the above results, the novel compound was found to show higher antibacterial effects against most of the above bacteria than the conventional antibacterial agent BPHB. Although triclosan has the strongest antibacterial effect, it is refrained from using as it is a halide compound and thus is concerned about effects to the environment and human body.

Hereinafter, the antibacterial agent prepared in Example 3 was used to prepare cosmetic products, food products and oral products having the following compositions.

Example 6

| Tooth paste (unit: % by weight) | |
|---|---|
| Dicalcium phosphate | 10.0 |
| Lauryl Sodium sulfate | 2.0 |
| Sodium carboxymethylcellulose | 0.5 |
| Saccharin sodium | 0.02 |
| Mint flavor | 1.0 |
| Antibacterial agent | 0.05% |
| Glycerine | Optimum quantity |
| | 100.0 |

Example 7

| Mouth wash (unit: % by weight) | |
|---|---|
| Ethyl alcohol | 10.0 |
| Polyoxyethylene hydrogenated castor oil | 2.0 |
| Mint flavor | 0.5 |
| Saccharin sodium | 0.02 |

-continued

Mouth wash (unit: % by weight)

| | |
|---|---|
| Glycerine | 10.0 |
| Pigment | Optimum quantity |
| Antibacterial agent | 0.25 |
| Purified water | Optimum quantity |
| | 100.0 |

Example 8

Candy (unit: % by weight)

| | |
|---|---|
| Powdered sugar | 50.0 |
| Starch syrup | 33.0 |
| Citric acid | 1.0 |
| Antibacterial agent | 0.25 |
| Purified water | Optimum quantity |
| | 100.0 |

Example 9

Chewing gum (unit: % by weight)

| | |
|---|---|
| Gum substrate | 21.0 |
| Powdered sugar | 63.9 |
| Corn starch | 12.5 |
| Lemon flavor | 1.0 |
| Acidifying agent | 0.6 |
| Antibacterial agent | 1.0 |
| | 100.0 |

Example 10

Lozenge (unit: % by weight)

| | |
|---|---|
| Starch | 98.45 |
| Powdered mint flavor | 0.8 |
| Sucrose fatty acid ester | 0.5 |
| Antibacterial agent | 0.25 |
| | 100.0 |

Example 11

Sanitizer (unit: % by weight)

| | |
|---|---|
| Ethanol | 20.0 |
| Antibacterial agent | 5.0 |
| Purified water | Optimum quantity |
| | 100.0 |

Example 12

Powdered detergent (unit: g)

| | |
|---|---|
| Lauryl, stearyl sodium sulfate | 15.0 |
| Sodium carbonate | 15.0 |
| Sodium metasilicate | 13.0 |
| Sodium citrate | 15.0 |
| Carboxymethylcellulose | 2.0 |
| Sodium sulfate | 38.0 |
| Musk tree perfume | 1.0 |
| Antibacterial agent | 1.0 |
| | 100.0 |

Example 13

Anhidrotic (unit: g)

| | |
|---|---|
| PEG-7 glyceryl cocoate | 2.0 |
| Hydrogenated oil | 5.0 |
| Myristyl myristate | 15.0 |
| Cyclomethycone | 33.5 |
| Stearyl alcohol | 20.0 |
| Stearyl isononenoate | 3.0 |
| Aluminum chrolohydrate | 20.0 |
| Fragrance ingredient for anhidrotic | 0.5 |
| Antibacterial agent | 1.0 |
| | 100.0 |

Example 14

Emollient cream (unit: g)

| | |
|---|---|
| Cetyl alcohol | 5.0 |
| Stearic acid | 3.0 |
| Vaseline | 5.0 |
| Squalane | 10.0 |
| Glycerol tri 2-ethyl hexanoate ester | 7.0 |
| Dipropylene glycol | 5.0 |
| Glycerine | 5.0 |
| Propylene glycol monostearate ester | 3.0 |
| POE(20) cetyl alcohol ether | 3.0 |
| Triethanolamine | 1.0 |
| Paraben | 0.3 |
| Fragrance ingredient for cream | 1.0 |
| Antibacterial agent | 1.0 |
| Purified water | Optimum quantity |
| | 100.0 |

Example 15

Shampoo (unit: g)

| | |
|---|---|
| Sodium laureth sulfate | 40.0 |
| Sodium cocoamphoacetate | 10.0 |
| Cocamide DEA | 2.0 |
| Butylene glycol | 2.0 |

-continued

| Shampoo (unit: g) | |
|---|---|
| Citric acid | 0.35 |
| Sodium chloride | 0.1 |
| Paraben | 0.3 |
| Tetrasodium EDTA | 0.1 |
| Fragrance ingredient for shampoo | 0.5 |
| Antibacterial agent | 1.0 |
| Purified water | Optimum quantity |
| | 100.0 |

Example 16

| Juice-containing beverage (unit: g) | |
|---|---|
| Fructose/glucose liquid sugar | 107.0 |
| Citric acid | 1.0 |
| Sodium citrate | 0.3 |
| Concentrated orange juice | 51.8 |
| Water-soluble orange flavor | 1.0 |
| Antibacterial agent | 0.1 |
| Water | Optimum quantity |
| | 1000.0 |

Example 17

| Sports drink (unit: g) | |
|---|---|
| Sugar | 31.0 |
| Glucose | 15.7 |
| Citric acid | 1.0 |
| Calcium lactate | 0.679 |
| Sodium citrate | 0.3 |
| Sodium chloride | 0.28 |
| Potassium chloride | 0.22 |
| Vitamin C | 0.864 |
| Sodium L-glutamate | 0.03 |
| Niacin | 0.013 |
| Calcium pantothenate | 0.007 |
| Vitamin B6 | 0.0022 |
| Vitamin B12 | 0.000006 |
| Lemon flavor | 1.0 |
| Antibacterial agent | 0.1 |
| Purified water | Optimum quantity |
| | 1000.0 |

Example 18

| Coffee milk beverage (unit: g) | |
|---|---|
| Regular coffee | 50.0 |
| Caster sugar | 50.0 |
| Milk | 150.0 |
| Emulsifying agent (fatty acid ester) | 0.5 |
| Coffee flavor | 1.0 |
| Milk flavor | 0.8 |

-continued

| Coffee milk beverage (unit: g) | |
|---|---|
| Antibacterial agent | 0.1 |
| Purified water | Optimum quantity |
| | 1000.0 |

Example 19

| Carbonated drink (unit: g) | |
|---|---|
| Fructose/glucose liquid sugar | 127.0 |
| Citric acid | 1.24 |
| Purified water | 200.0 |
| Lemon flavor | 0.12 |
| Antibacterial agent | 0.05 |
| Carbonated wate | Optimum quantity |
| | 1000.0 |

Example 20

| Juice-containing jelly (unit: g) | |
|---|---|
| Apple juice | 6.0 |
| Starch syrup | 3.5 |
| Caster sugar | 13.0 |
| Malic acid | 0.21 |
| Gelling agent | 0.9 |
| Sodium citrate | 0.05 |
| Caramel pigment | 0.08 |
| Apple flavor | 0.2 |
| Antibacterial agent | 0.01 |
| Purified water | Optimum quantity |
| | 100.0 |

Example 21

| Lemon tea (unit: g) | |
|---|---|
| Tea leaf extract (brix 1.0) | 200.0 g |
| Caster sugar | 60.0 |
| Lemon concentrated juice | 1.56 |
| Vitamin C | 0.1 |
| Antibacterial agent | 0.05 |
| Purified water | Optimum quantity |
| | 1000.0 |

No turbidity or sediment was visually found in the acidic beverages prepared above (Examples 16, 17, 19 and 21).

The antibacterial agent obtained according to the present invention has an improved antibacterial effect. Specifically, it exerts improved antibacterial activity against various bacteria including oral-related bacteria such as cariogenic bacteria and periodontal bacteria, food poisoning bacteria and putrefactive bacteria concerned in the food industry, and acne bacteria, dandruff-causative bacteria and resident skin bacteria concerned in the cosmetic industry. Thus, the present antibacterial agent can be applied to wide variety of products such as food products, cosmetic products (fragrance products, skin-care cosmetics, hair-care cosmetics, toiletry products, bath additives, body-care products, detergents, softeners, aromatic deodorants), oral products and pharmaceutical products.

Furthermore, the antibacterial agent of the present invention may be used with other antibacterial agents or substances having antibacterial activities and thus synergistic antibacterial effect thereof can be expected. By using the antibacterial agent of the present invention in the above-mentioned products, improved antibacterial effect and preservation stability can be provided.

The invention claimed is:

1. A purified, synthesized, and/or isolated compound 9-(1', 5'-dimethyl-1'-vinyl-4'-hexenyl)-4-hydroxy-7H-furo[3,2-γ][1]benzopyran-7-one.

2. An antibacterial agent comprising the compound of claim 1.

3. A food product comprising the antibacterial agent of claim 2.

4. An oral product comprising the antibacterial agent of claim 2.

5. A cosmetic product comprising the antibacterial agent of claim 2.

6. A pharmaceutical product comprising the antibacterial agent of claim 2.

7. A method for producing a compound 9-(1',5'-dimethyl-1'-vinyl-4'-hexenyl)-4-hydroxy-7H-furo[3,2-γ][1]benzopyran-7-one, comprising the steps of:

dissolving 4-(1',5'-dimethyl-1'-vinyl-4'-hexeneoxy)-7H-furo[3,2-γ][1]benzopyran-7-one in a high-boiling organic solvent; and agitating the resultant while heating in an inert gas atmosphere.

8. A method for producing a compound 9-(1',5'-dimethyl-1'-vinyl-4'-hexenyl)-4-hydroxy-7H-furo[3,2-γ][1]benzopyran-7-one, comprising the steps of:

dissolving a compound 3-[6'-(3",7"-dimethyl-2",6"-octadieneoxy)-4'-hydroxy-5'-benzofuranyl]-propenoic acid alkylester having a phenolic hydroxyl group protected with a protective group in a high-boiling organic solvent; agitating the resultant while heating in an inert gas atmosphere; and removing the protective group.

* * * * *